United States Patent
Sikdar et al.

(10) Patent No.: US 10,935,645 B2
(45) Date of Patent: Mar. 2, 2021

(54) METHOD AND APPARATUS FOR LOW-POWER ULTRAPORTABLE ULTRASOUND IMAGING

(71) Applicant: George Mason University, Fairfax, VA (US)

(72) Inventors: Siddhartha Sikdar, Washington, DC (US); Parag Chitnis, Fairfax, VA (US); Nima Akhlaghi, Sterling, VA (US); Elizabeth Tarbox, Nokesville, VA (US); Paul Otto, Lorton, VA (US); Paul Gammell, Exmore, VA (US)

(73) Assignee: GEORGE MASON UNIVERSITY, Fairfax, VA (US)

( * ) Notice: Subject to any disclaimer, the term of this patent is extended or adjusted under 35 U.S.C. 154(b) by 555 days.

(21) Appl. No.: 15/793,969

(22) Filed: Oct. 25, 2017

(65) Prior Publication Data
US 2018/0113205 A1  Apr. 26, 2018

Related U.S. Application Data

(60) Provisional application No. 62/412,568, filed on Oct. 25, 2016.

(51) Int. Cl.
*G01S 7/52* (2006.01)
*G01N 29/06* (2006.01)
(Continued)

(52) U.S. Cl.
CPC ........ *G01S 7/52025* (2013.01); *A61B 8/5207* (2013.01); *A61B 8/54* (2013.01);
(Continued)

(58) Field of Classification Search
CPC ........ G01S 7/52; G01S 15/89; G01S 15/8977; G01S 15/8913; G01S 15/8954; G01S 7/52025; G01S 15/8915; G01S 7/52096; A61B 8/00; A61B 8/54; A61B 8/5207; A61B 8/4494; G01N 29/06; G01N 29/26; G01N 29/42; G01N 29/07; G01N 29/262; G01N 29/348; G01N 29/265; G01N 29/0672
See application file for complete search history.

(56) References Cited

U.S. PATENT DOCUMENTS 4,568,877 A * 2/1986 Tinsley ............... G01R 19/155
323/266
5,269,309 A * 12/1993 Fort ....................... G01H 5/00
600/447
(Continued)

*Primary Examiner* — Hovhannes Baghdasaryan
*Assistant Examiner* — Amie M Ndure
(74) *Attorney, Agent, or Firm* — Ballard Spahr LLP

(57) ABSTRACT

Methods, systems, and apparatuses are disclosed for ultrasound imaging comprising Time Delay Spectrometry. A frequency swept signal can be transmitted through a medium, such as human tissue. The signal can be a low-voltage signal (e.g., 0 volts to 5 volts peak-to-peak) transmitted for long duration (e.g., 20 milliseconds) at various frequencies. As the signal propagates through the medium it can be reflected and delayed. A delay associated with the signal the can cause a change in the associated frequencies. The signal can be filtered to retain only frequencies in an audio frequency range. The signal can be beamformed and processed to produce an image.

20 Claims, 14 Drawing Sheets

(51) Int. Cl.
*G01S 15/89* (2006.01)
*G01N 29/26* (2006.01)
*G01N 29/34* (2006.01)
*G01N 29/42* (2006.01)
*A61B 8/08* (2006.01)
*G01N 29/07* (2006.01)
*G01N 29/265* (2006.01)
*A61B 8/00* (2006.01)

(52) U.S. Cl.
CPC ......... *G01N 29/0672* (2013.01); *G01N 29/07* (2013.01); *G01N 29/262* (2013.01); *G01N 29/265* (2013.01); *G01N 29/348* (2013.01); *G01N 29/42* (2013.01); *G01S 15/8913* (2013.01); *G01S 15/8915* (2013.01); *G01S 15/8954* (2013.01); *G01S 15/8977* (2013.01); *A61B 8/4494* (2013.01); *G01S 7/52096* (2013.01)

(56) References Cited

U.S. PATENT DOCUMENTS

| | | | | |
|---|---|---|---|---|
| 5,549,111 A * | 8/1996 | Wright | ................. | G01S 15/895 600/443 |
| 5,904,652 A * | 5/1999 | Gilbert | ..................... | A61B 8/56 600/447 |
| 6,248,073 B1 * | 6/2001 | Gilbert | .................. | A61B 8/463 600/443 |
| 9,729,077 B2 * | 8/2017 | Stein | ....................... | H02H 3/20 |
| 2017/0105706 A1 * | 4/2017 | Berger | ................ | A61B 8/4472 |

\* cited by examiner

METHOD AND APPARATUS FOR LOW-POWER ULTRAPORTABLE ULTRASOUND IMAGING

CROSS REFERENCE TO RELATED PATENT APPLICATION

This application claims priority to U.S. Patent Application No. 62/412,568 filed Oct. 25, 2016, which is herein incorporated by reference in its entirety.

GOVERNMENT SUPPORT CLAUSE

This invention was made with government support under CNS1329829 awarded by the National Science Foundation. The government has certain rights in the invention.

BACKGROUND

Ultrasound imaging is routinely performed using pulse echo signaling techniques. Pulse echo signaling requires a high voltage, high frequency (e.g., short duration ultrasound) pulsed signal to be sent through tissue to generate images. As such, low-noise amplifiers and digitizers capable of handling high frequencies (e.g., megahertz) are required. Such high-performance components consume excessive amounts of power and are not easily implemented in scenarios where resources may be scarce (e.g., low and middle-income countries). There is a need for ultrasound imaging that can be implemented on components that operate at lower frequencies and thus require less power (e.g. components that can be operated via battery power rather than by a commercial power outlet). These and other shortcomings are addressed by the present disclosure.

SUMMARY

It is to be understood that both the following general description and the following detailed description are exemplary and explanatory only and are not restrictive. Methods, systems, and apparatuses are disclosed for low-power, portable, ultrasound imaging. The methods, systems, and apparatuses disclosed can use time delay spectrometry for low-power, portable, ultrasound imaging.

The methods, systems, and apparatuses disclosed can transmit a frequency swept signal through a medium, such as human tissue, for example. Instead of a high-voltage (e.g., 100 V peak-to-peak) signal transmitted in short duration (e.g., 200 nanoseconds) pulses, phased array transducers can be used to transmit low-voltage signals (e.g., 0 volts to 5 volts peak-to-peak) for long duration (e.g., 20 milliseconds) at various frequencies (e.g., frequency sweeps from 5-10 MHz). As the signal propagates through tissue it can be reflected and delayed. A delay associated with the signal can cause a change in the associated frequencies. The signal can be filtered to retain only frequencies in an audio frequency range. The signal can be beamformed and processed to produce an image.

Additional advantages will be set forth in part in the description which follows or may be learned by practice. The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Figure 1:
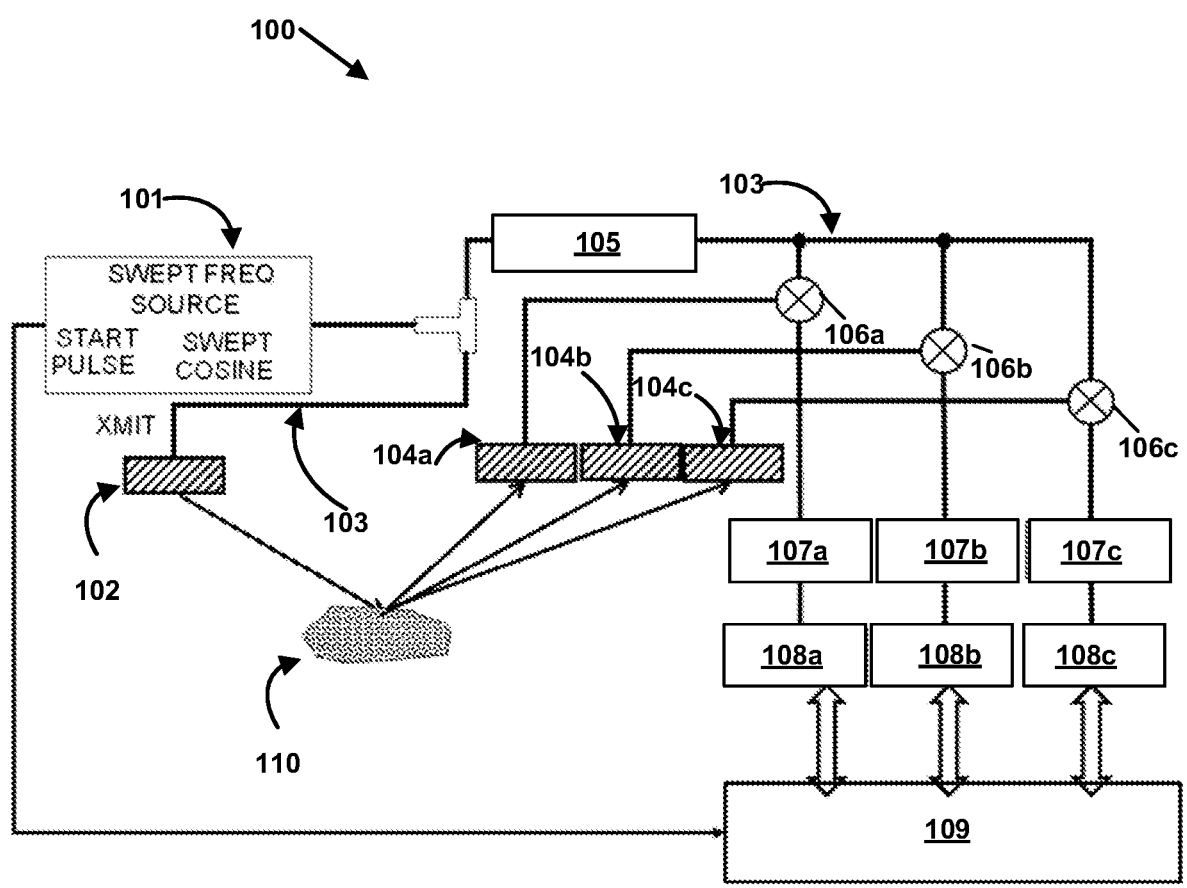
FIG. 1 shows a block diagram of a Time Delay Spectrometry (TDS) data acquisition system.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Throughout the specification, an "ultrasound image" can refer to an image of an object, which is obtained using ultrasound waves. Furthermore, an "object" may be a human, an animal, or a part of a human or animal (e.g., tissue). For example, the object may be an organ (e.g., the liver, the heart, the brain, the abdomen, and the like), a blood vessel, or a combination thereof. Also, the object may be a phantom. The phantom means a material having a density, an effective atomic number, and a volume that are approximately the same as those of an organism.

The present disclosure relates to methods, systems, and apparatuses for ultrasound imaging. For example, the methods, systems, and apparatuses disclosed are for low-power, portable, ultrasound imaging. The methods, systems, and apparatuses disclosed can use time delay spectrometry for low-power, portable, ultrasound imaging. The methods, systems, and apparatuses disclosed can transmit a frequency swept signal through a medium such as human tissue, for example. Instead of a high-voltage (e.g., 100 V peak-to-peak) signal transmitted in short duration (e.g., 200 nanoseconds) pulses, phased array transducers can be used to transmit a low-voltage signal (e.g., 0 volts to 5 volts peak-to-peak) for a long duration (e.g., 20 milliseconds) at various frequencies (e.g., frequency sweeps from 5-10 MHz). As the signal propagates through the medium it can be reflected (e.g., reflected by tissue/medium, reflected by a reflective element placed in the medium, etc. . . . ) and delayed. A delay associated with the signal can cause a change in frequencies associated the signal. The change in frequency can be from a megahertz range (e.g., 5-10 Mhz) to a kilohertz range (e.g., radio frequency range). The signal can be filtered (e.g., down mixed to remove a carrier frequency) and frequencies in the audio frequency range can be beamformed and processed (e.g., via Fourier Transformations) to produce an image. The use of a low-voltage signal enables the methods, systems, and apparatuses disclosed to employ inexpensive low-power components. For example, transducers with a low transmit efficiency (e.g., ability to convert electrical voltage to pressure) can be used. Such transducers can be made of co-polymer materials such as poly[vinylidenefluoride-trifluoroethylene] (P[VDF-TrFE]). As such, the methods, systems, and apparatuses disclosed inherently operate via low power. Beamforming contributes to producing images comparable to conventional diagnostic ultrasound imaging systems.

Time Domain Spectrometry (TDS) with Phased Array

FIG. 1 is a block diagram of a time delayed spectrometry (TDS) system 100. Those skilled in the art will appreciate that present methods, systems, and apparatuses can employ both digital and analog equipment. One skilled in the art will appreciate that provided herein is a functional description and that the respective functions may be performed by software, hardware, or a combination of software and hardware. The system 100 can comprise a signal source 101, a source transducer 102, an ultrasound propagation path 103, a receiving transducer 104*a,b,c*, and supporting electronics such as an attenuator 105, frequency mixers 106*a,b,c*, filters 107*a,b,c*, digitizers 108*a,b,c*, a digital signal processor 109, and a reflector 110. The system 100 can include other components. A source signal can be transmitted from the signal source 101. Without loss of generality the source signal is assumed to be a linear, swept-frequency cosine wave denoted by $\cos(\omega t)$, that is swept at the rate of $S/2\pi$ Hertz per second. Thus the time dependence of the instantaneous frequency is $\omega=2\pi f=St$, where f represents a frequency, S represents the constant sweep rate, and t represents the time from a beginning of a sweep. Notably, St is the source signal used to interrogate the system 100. Further, St is used instead of ω as a reminder that it is not at a constant frequency. The source signal can be applied to a source transducer 102 and transmitted through the system 100 via the ultrasound propagation path 103. The source signal can be reflected (e.g., bounce off) a reflector 110. The reflector 110 can be an object such as tissue or a reflective object placed in tissue. Reflection of the source signal can cause it to be time delayed. An ultrasound frequency of a final time delayed spectrometry (TDS) signal (e.g., received signal, signal received by a second set of phased array transducers) that represents a response can be received by the receiving transducer 104*a,b,c*. The receiving transducer 104*a,b,c* can be a phased array transducer. The final time delayed spectrometry (TDS) signal (e.g., received signal) can be denoted as Sr.

The received signal, Sτ, is a version of the transmitted signal, St, that is modified by the frequency response of the system. A magnitude (e.g., power) of the signal can be represented by (A). Thus A(St). As such, A(ω)≡A(St). Sτ represents St delayed by a propagation time through a medium (e.g., tissue). Further $t_D \equiv \tau = z/c$ where c is the speed of sound, and z is the length of the ultrasound path. As such, an output (Y(ω)) of the system 100 can be represented as:

$$Y(\omega)=|A(St)|\cos[(St-S\tau)t+\varphi_A(St)], \quad (1)$$

where A(St) is the system response with magnitude |A(St)|, and phase $\varphi_A(St)$, $S\tau=2\pi\Delta f=2\pi St_D$ is the TDS offset frequency. Since an up-sweep is assumed, the offset frequency $S\tau=2\pi\Delta f$ is negative in Equation (1). It would be positive for the case of a down-sweep. As such, the absolute value is taken, such as |A(St)|, for example.

The output Y(ω) of the system 100 can be the received signal mixed with (e.g., multiplied by) the source signal. For example, cos(ωt)=cos [(St)t]. The output Y(ω) of the system 100 can be the received signal mixed with the source signal by the frequency mixers 106*a,b,c*. The frequency mixers 106*a,b,c* can be configured to mix (e.g., multiple) one or more signals. The output of the frequency mixers 106*a,b,c* can contain components at the sum and difference frequencies, $$2Y(St)\cos[(St)t]=|A(\cos[(St)t]|\{\cos[(2St-S\tau t+\varphi_A(S\tau)]+\cos[S\tau t-\varphi_A(St)]\} \quad (2)$$

where an identity equation cos α cos β=(½) [cos(α+β)+cos (α−β)] has been used, and where the number 2, which arises from the trigonometry identities, has been moved to the left to simplify notation. The mixed signal can then be passed to the filters 107*a,b,c*. The filters 107*a,b,c* can be filters low-pass filters that remove the sum-frequency component and retain the difference-frequency component, to produce a "dechirped" signal. The dechirped signal (e.g., a signal where frequency increases or decreases have been removed) can be represented as:

$$2D(St)=|A(St)|\cos[S\tau t-\varphi_A(St)]. \quad (3)$$

The dechirped signal can be a sinusoidal signal with a constant frequency (f) that is equal to Sτ/2π, where S represents the constant sweep rate and τ represents the time delay of the system (e.g., $t_D = r = z/c$). The time scale, t, of D(St) can represent the ultrasound frequency at which the system was interrogated, being given by ω=2πf=St. Notable, since this constant frequency is proportional to the time delay, the range of a reflector (e.g., how deeply imbedded the reflector is in tissue, how deep the target object in tissue is, etc. . . . ) can be determined by simply measuring the frequency of D(St).

The signal propagation described assumes a single time delay (e.g., $t_D = \tau = z/c$) that corresponds to a single ultrasound path (e.g., ultrasound propagation path 103). The system 100 can include several propagation paths. The several propagation paths can be associated with various/different time delays. Dechirped signals associated with several propagation paths and various/different time delays can be summed and represented as:

$$2D(St)=\Sigma D_i(St)=\Sigma |A_i(St)|\cos[S\pi_i t-\varphi_{Ai}(St)]. \quad (4)$$

where Σ represents the sum of the responses to each path of the several propagation paths, each with a response $D_i(St)$. The response of each path can be represented by a magnitude (e.g., $|A_i(St)|$), phase (e.g., $\varphi_{Ai}(St)$), and propagation delay (e.g., $\tau_i$). Each path delay can be represented by its respective frequency $S\tau_i$ in the composite signal. Each component of D(St) that has a different time delay can have a different frequency. Components of D(St) with time delays that are larger or smaller than a desired range can be eliminated by filtering (e.g., filtering via filters 107*a,b,c*, band-pass filtering) D(St).

A component i of D(St) can be represented by $|A_i(St)|\cos[S\tau_i t-\varphi_{Ai}(St)]$. A Fourier Transform of D(St) can be performed to obtain a response at position $S\tau_i/2\pi$ Hz of a transformed axis, which represents a delay time, with amplitude $|A_i(St)|$ and phase $\varphi_{Ai}(St)$. The result can be a signal that is smoother (e.g., with less noise and error) with improved resolution than a conventional absolute value ("rectified") signal.

The receiving transducer 104 can be a phase array transducer. The elements (e.g., arrays) can be adjacent or not adjacent. For example, arrays that are not necessarily adjacent can arbitrarily be called "1" and "2". To implement a phased array of the receiving transducer 104, the time delay of each receiving element can be adjusted. The time delay of each receiving element can be adjusted so that the adjusted signals will be in phase (e.g., for a given steering angle) and can be added. As such, the time delay of an element can be represented as:

$$\tau_2=\tau_1+(\tau_2-\tau_1)=\tau_1+\tau_{12} \quad (5)$$

where $\tau_{12}=(\tau_2-\tau_1)$ is simply the difference between the propagation times of arrays (e.g., paths) 2 and 1.

Given the substitution, for a case of a single time delay, such as represented by Eq (3), for these two elements can be represented as:

$$2D_1(St)=|A_1(St)|\cos[S\tau_1 t-\varphi_{Ai}(St)]; \text{ and}$$

$$2D_2(St)=|A_2(St)|\cos[S(\tau_1+\tau_{12})t-\varphi_{A2}(St)]. \quad (6)$$

$D_2(St)$ can be multiplied by an offset frequency $\cos(S\tau_0 t)$. Multiplying $D_2(St)$ by an offset frequency $\cos(S\tau_0 t)$, taking only the lower sideband (i.e., the difference frequency), and using the same trigonometric identities as used in deriving equation 2, can results in the following:

$$4D_2(St)=|A_2(St)|\cos[S(\tau_1+\tau_{12}-\tau_0)t-\varphi_{A2}(St)]. \quad (7)$$

which is equal to the original $D_2(St)$ shifted in frequency by the amount $S\tau_0$. If $\tau_0$ is chosen to equal $\tau_{12}$ then the time difference between the signals to elements 1 and 2 is cancelled and can be represented as:

$$4D_2(St)=|A_2(St)|\cos[S\tau_1 t-\varphi_{A2}(St)]. \quad (8)$$

which will can be added in phase with the signal of element 1 (e.g., array 1). All elements of the receiving transducer 104*a,b,c* can be added. For each steering angle a different set of values of $\tau_0$ for each element can be chosen.

Notably, the filters 107a,b,c may not be required are not required to eliminate one of the sidebands if the frequency is shifted by quadrature multiplication. Further, with an analog implementation of the system 100 the channels can be matched to achieve complete cancellation of an undesired sideband (e.g., the difference frequency).

Production of either one of the sidebands (e.g., sum frequency, difference frequency) can be done without filters (filters 107a,b,c) using quadrature multiplication. Quadrature multiplication of frequency shifting can be done by performing four multiplications using the original signal St and a Hilbert transformation of the original signal as two multiplicands and a sine and cosine at the offset frequency as the pair of multipliers. The result can be four product signals or vectors. An appropriate sum or difference of the products can be used to produce an upper sideband (e.g., sum frequency) of the signal, a Hilbert transform of the upper sideband of the signal, a lower sideband (e.g., difference frequency), or a Hilbert transform of the lower sideband of the signal.

The digitizers 108a,b,c, can be used to digitize the outputs of the filters 107a,b,c. For example, for each sweep (e.g., frequency sweep by the signal source 101) the digitized "dechirped" signal from each receiving transducer 104a,b,c can be been stored. As such, a sweep from the signal source 101 can have a set of arrays (vectors). Each array can be associated with a "dechirped" signal which represents the spectra received by a particular receiving transducer 104a, b,c. The set of arrays (vectors) from any sweep can contain all of the information required to produce an ultrasound image of an object at the time of the sweep. The data can be processed by the digital signal processor 109 to produce a set of scanlines or "looks" in each direction. The scanlines can be combined to produce an image.

Imaging

Data (e.g., output from the receiving transducer 104a,b,c) can be processed by the digital signal processor 109 to produce a set of scanlines or "looks" in each direction. The scanlines can be combined to produce an image. For each direction (e.g., "look", steering angle, etc.) the methods and systems previously described can be used to combine the signals from the digitizers 108a,b,c (e.g., output from the receiving transducer 104a,b,c) to produce a spectra of a signal St received from the respective direction. The result is a spectra (e.g., $\Sigma D_i(St)$) for the "look" in the respective direction. As previously described, a Fourier transform of the signal St received from the respective direction can produce a time record of the arrival of energy from the respective direction. Such can be referred to as an "A-mode" signal. Such the information can be used to produce a single scan line. For example, the direction of the scan line can be based on the steering angle and a distance along the scan line can be an axis of a respective Fourier transform.

The process can be repeated for each steering angle to produce a complete set of scan lines required to produce an image. Further, because the Fourier transform magnitude is the magnitude of the analytic signal, an image produced can be more accurate than an image obtained by full wave rectification of a pulsed signal. Note, any of the described steps or operations can be performed serially or in parallel.

Phasing a Transmit Signal

Figure 2:
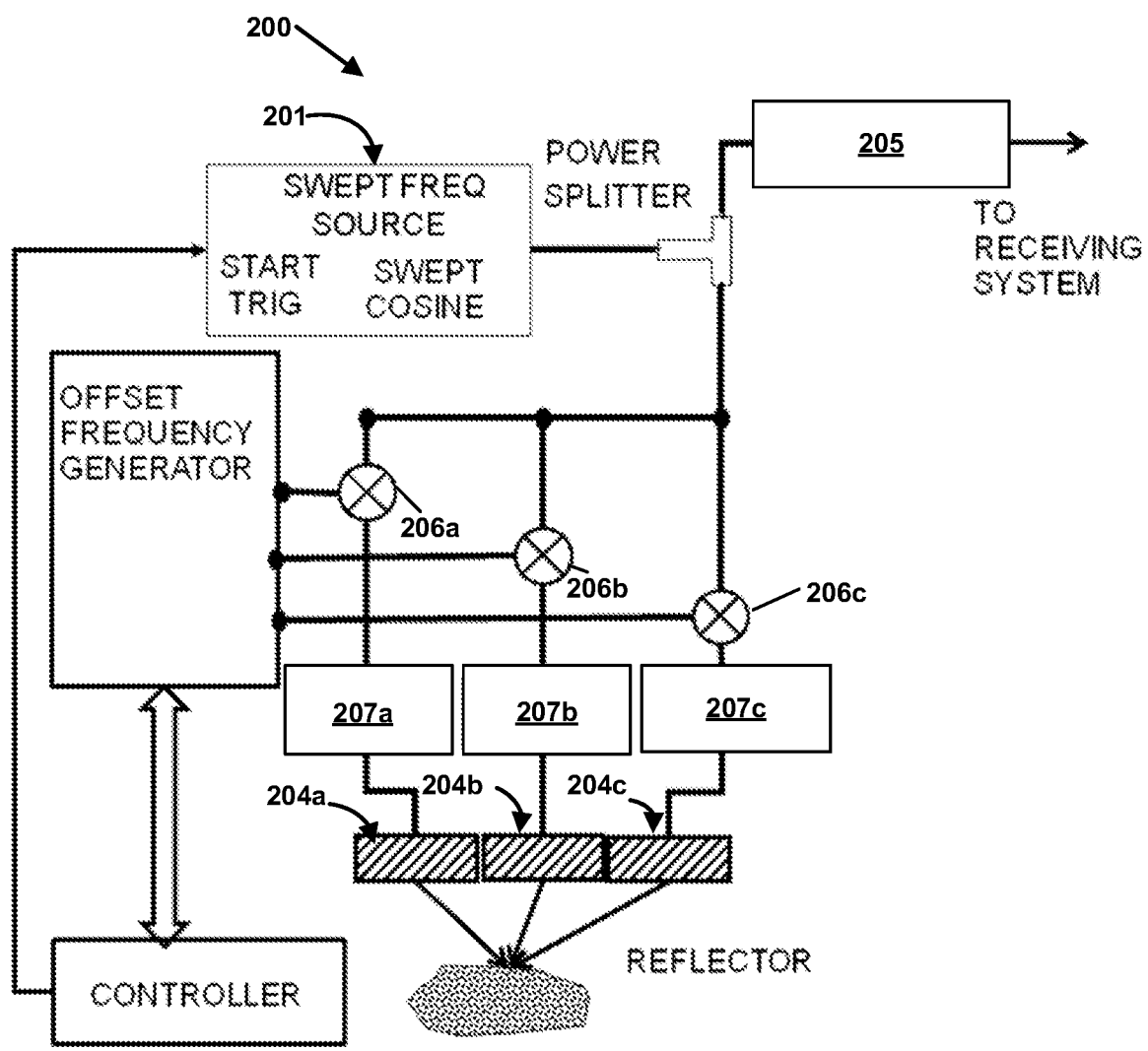
FIG. 2 is an example scheme of transmit phasing with TDS by using frequency offsets.

FIG. 2 is a block diagram of a system 200 for phasing of a transmit array using time delayed spectrometry (TDS). The system 200 can comprise a signal source 201, a receiving transducer 204a,b,c, and supporting electronics such as an attenuator 205, frequency mixers 206a,b, and filters 207a, b,c. The system 200 can comprise additional components.

The signal source 201 can provide signal with a frequency that is swept linearly in time (e.g., time offset). The required time offset can be provided by the offset frequency generator 202 by frequency offsetting the swept signal provided by the signal source 201. For each steering angle, the offset frequency generator 202 can provide a set of signals each a different frequency (e.g., a frequency appropriate for an element). However, after a propagation time delay, the signal from each element can be in phase.

The signal source 201 can simultaneously generate two swept signals that are 90 degrees out of phase with each other (e.g. a sine and a cosine wave). Due to the implementation of the offset frequency generator 202 the offset sweeps can be generated without the need of filters. For example, generation of a sine and cosine pair at each offset frequency is straightforward. With a sine and cosine swept frequency and also a sine and cosine offset frequency; the shifted sweep can be generated without a superfluous sideband using the quadrature technique previously described. For example, the product of the cosine sweep and a cosine offset frequency summed with the product of a sine sweep and a sine offset frequency can yield a signal at is a difference of the two frequencies. Further, subtracting such products can produce a signal at the sum of the two frequencies. The system 200 can comprise both digital and analog components.

The range of a reflector 203 (e.g., tissue) can be followed in real time by tracking the frequency of a dechirped signal of equation (3). In an aspect, the angular position of an object (e.g., reflector 203) can be tracked in real time by a feedback that adjusts the offsets so that the steering angle will follow the angular position of an object. Such can be tracked in real time.

In an aspect, time delayed spectrometry (TDS) can provide both Doppler and ranging information by combining the signals from an up-sweep (e.g., up-chirp) and a down-sweep (e.g., down-chirp). For example, a dechirped signal from an up sweep can be represented as:

$$2Du(St)=|A(\omega)| \cos [(\Delta\omega_d-\Delta\omega_r)t-\varphi_A(\omega)] \quad (9)$$

where $\Delta\omega_d$ is the frequency shift due to the Doppler shift. The respective value can be positive for approaching reflectors and negative for receding reflectors. Further, $\Delta\omega_r$ can represent the frequency shift due to the range. As a further example, a dechirped signal for a down sweep can be represented as:

$$2Dd(St)=|A(\omega)|\cos [\Delta\omega_d+\Delta\omega_r)t-\varphi_A(\omega)] \quad (10)$$

Multiplying (e.g., mixing via the frequency mixers 206a, b,c) the dechirped signals from an up-sweep and a from a down-sweep can result in sidebands at the sum and difference frequencies of the original signals transmitted by the signal source 201. At the sum frequency, the shift due to the range can be filtered (e.g., canceled, removed) such that only the Doppler frequency remains. At the difference frequency, the Doppler shift can be filtered (e.g., canceled, removed) and the frequency is can be proportional to the frequency range.

Figure 3:
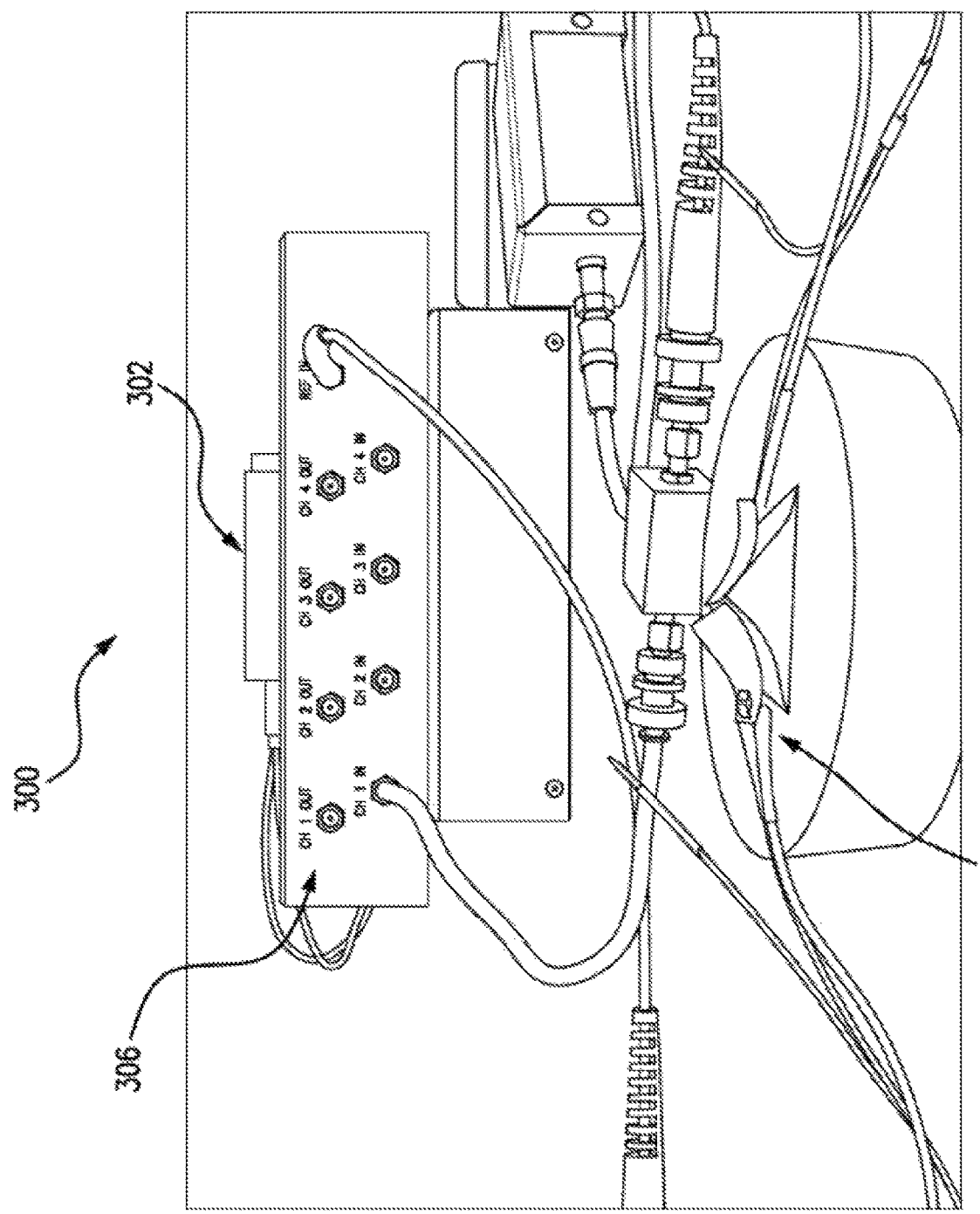
FIG. 3 illustrates a prototype comprising flexible transducers, a battery power source, and ultrasound electronics.

FIG. 3 illustrates a prototype of a time delayed spectrometry (TDS) system 300. The system 300 can comprise a battery power source 302, one or more flexible transducers 304, and ultrasound electronics 306. The ultrasound electronics 306 can comprise components such as an attenuator (e.g., attenuator 105), frequency mixers (e.g., frequency mixers 106a,b,c), filters (e.g., filters 107a,b,c), digitizers (e.g., digitizers 108a,b,c), and a digital signal processor (e.g., digital signal processor 109). The system 300 can comprise additional components associated with time delayed spectrometry (TDS).

Figure 4:
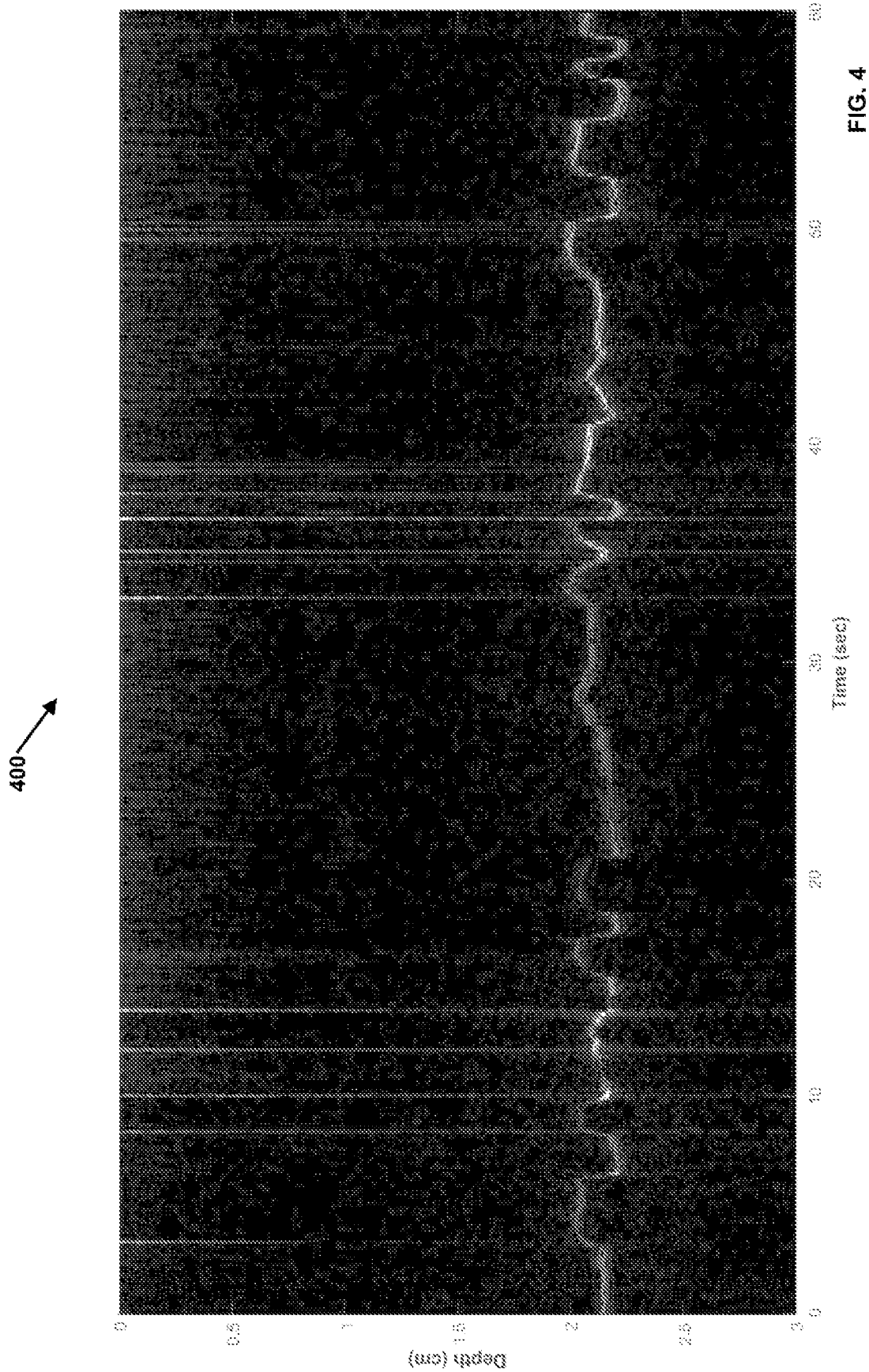
FIG. 4 illustrates an example real-time image of a moving interface.

FIG. 4 illustrates an example real-time image of a moving interface. The real-time image 400 can be derived from data (e.g., output from the receiving transducer 104*a,b,c*) from a time delayed spectrometry (TDS) system. A frequency swept source signal can be processed by the digital signal processor to produce a set of scanlines or "looks" in a plurality of directions. The scanlines can be combined to produce the image real-time image 400.

Figure 5:
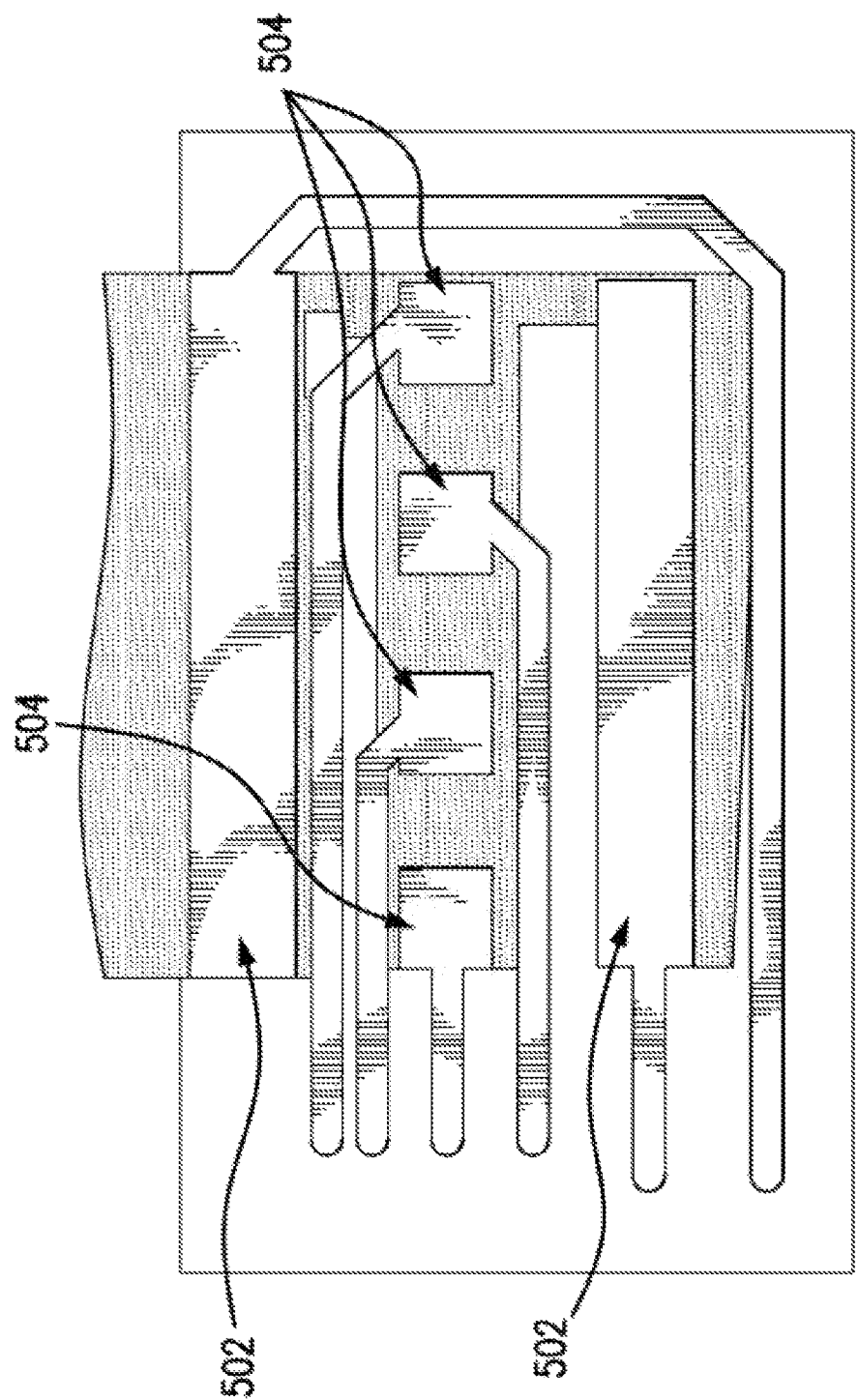
FIG. 5 is an example 2-channel transmit and 4-channel receive flexible PVDF transducer.

FIG. 5 an example 2-channel transmit and 4-channel receive flexible PVDF (poly [vinylidenefluoride-trifluoro-ethylene] (P[VDF-TrFE])) transducer 500. The transducer 500 can comprise 2-channel transmit element 502 and a 4-channel receive element 504. The PVDF transducer 500 can have a low transmit efficiency (e.g., ability to convert electrical voltage to pressure). The PVDF transducer 500 can be made of co-polymer materials such as poly [vinylidenefluoride-trifluoroethylene] (P[VDF-TrFE]). As such, the methods, systems, and apparatuses disclosed can use the PVDF transducer 500 to operate via low power.

Figure 6:
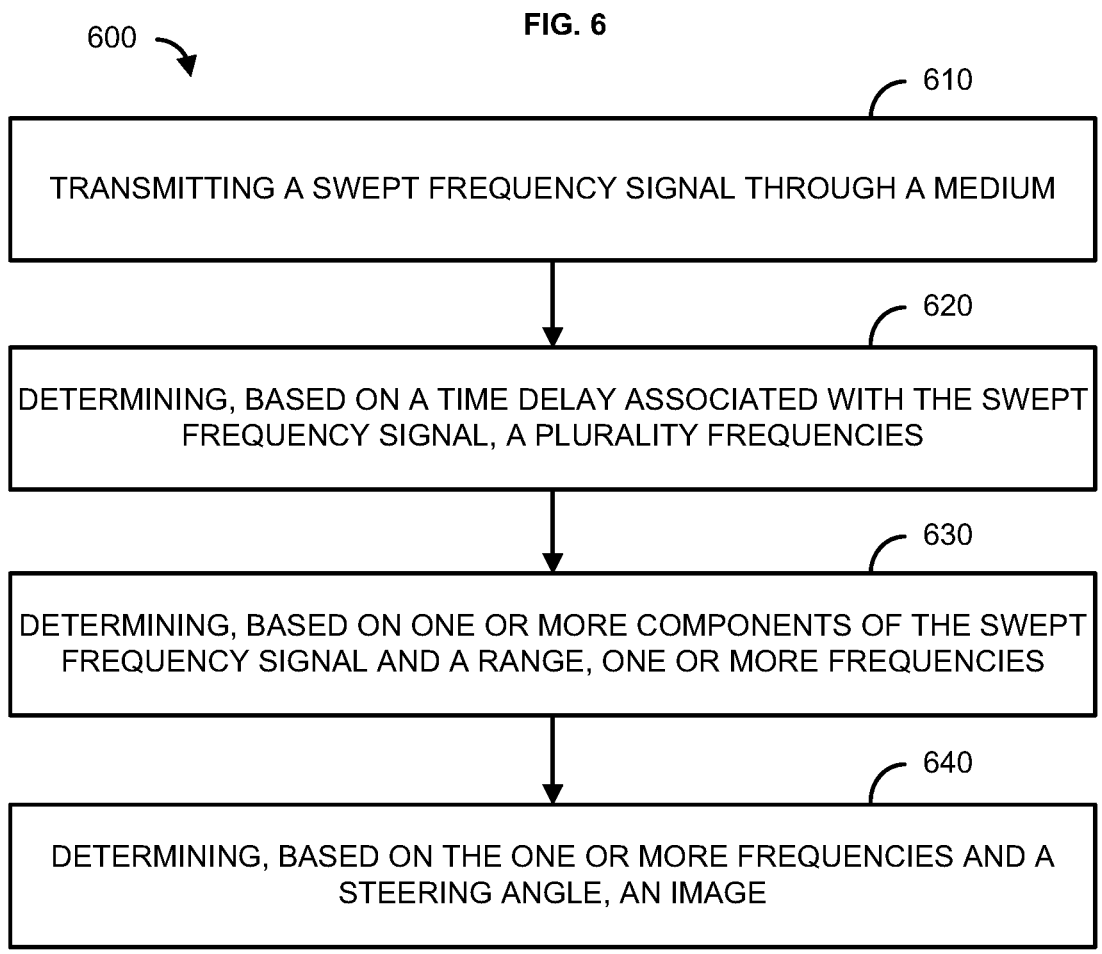
FIG. 6 is a flow chart of an example method.

FIG. 6 is a method for low-power, portable, ultrasound imaging. At step 610, a signal can be transmitted via a transmit channel of a transducer. The signal can be a swept frequency signal. The signal can be transmitted through a medium such as tissue (e.g., human tissue, an organ, a limb, etc.), for example.

At 620, a plurality of frequencies can be determined from the swept frequency signal. The plurality of frequencies can be determined based on a time delay associated with the swept frequency signal. The time delay associated with the swept frequency signal can be based the signal propagating through the medium.

At 630, one or more frequencies associated with the swept frequency signal can be determined. For example, a constant frequency can be determined (e.g., consistent frequency, carrier frequency, etc. . . . ). The constant frequency can be proportional to the time delay. One or more components of the swept frequency signal can be received via a receive channel of the transducer. Each component of swept frequency signal can have a different time delay due to the various frequencies used during a sweep. Components of the swept frequency signal with time delays that are larger or smaller than a desired range can be eliminated by filtering the signal (e.g., band-pass filtering).

At 640, an image can be determined. The image can be determined based on the one or more frequencies associated with the swept frequency signal and a steering angle. With a digital implementation, for each sweep the digitized "dechirped" signal from each receiving transducer has been stored. For example, the swept frequency signal can be received via a receive channel of the transducer. The receive channels of the transducer can be associated with a set of arrays (e.g., vectors). Each array can represent spectra of frequencies received by the particular channel of the receiving transducer. The set of arrays can contain contains all of the information required to produce an ultrasound image of the object. The arrays can be processed to produce a set of scanlines or "looks" in each direction of the arrays (vectors). The scanlines can be combined to produce an image. A Fourier transform can be used on the scanlines to generate an image. The image can be an electrical representation of a region of interest associated with a medium through which the swept frequency signal propagated.

The methods and systems can employ artificial intelligence (AI) techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the methods and systems. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

As described supra, Time Delay Spectrometry (TDS) is a signaling paradigm that can facilitate low-voltage transmit signals and simplified receiver electronics. In TDS, a low-voltage linearly swept chirp signal is transmitted into the medium and the backscattered received echo is frequency shifted based on the time delay to reflecting interfaces. The frequency shift can be recovered by demodulating the received signal with the (reference) transmit signal and low-pass filtering the demodulated signal. Fourier analysis of the filtered received signal can be used to recover the equivalent time-of-flight to reflecting interfaces. The receive electronics for TDS systems can therefore be thought to be analogous to a frequency modulated radio receiver with the additional step of applying the Fourier transform.

Figure 7:
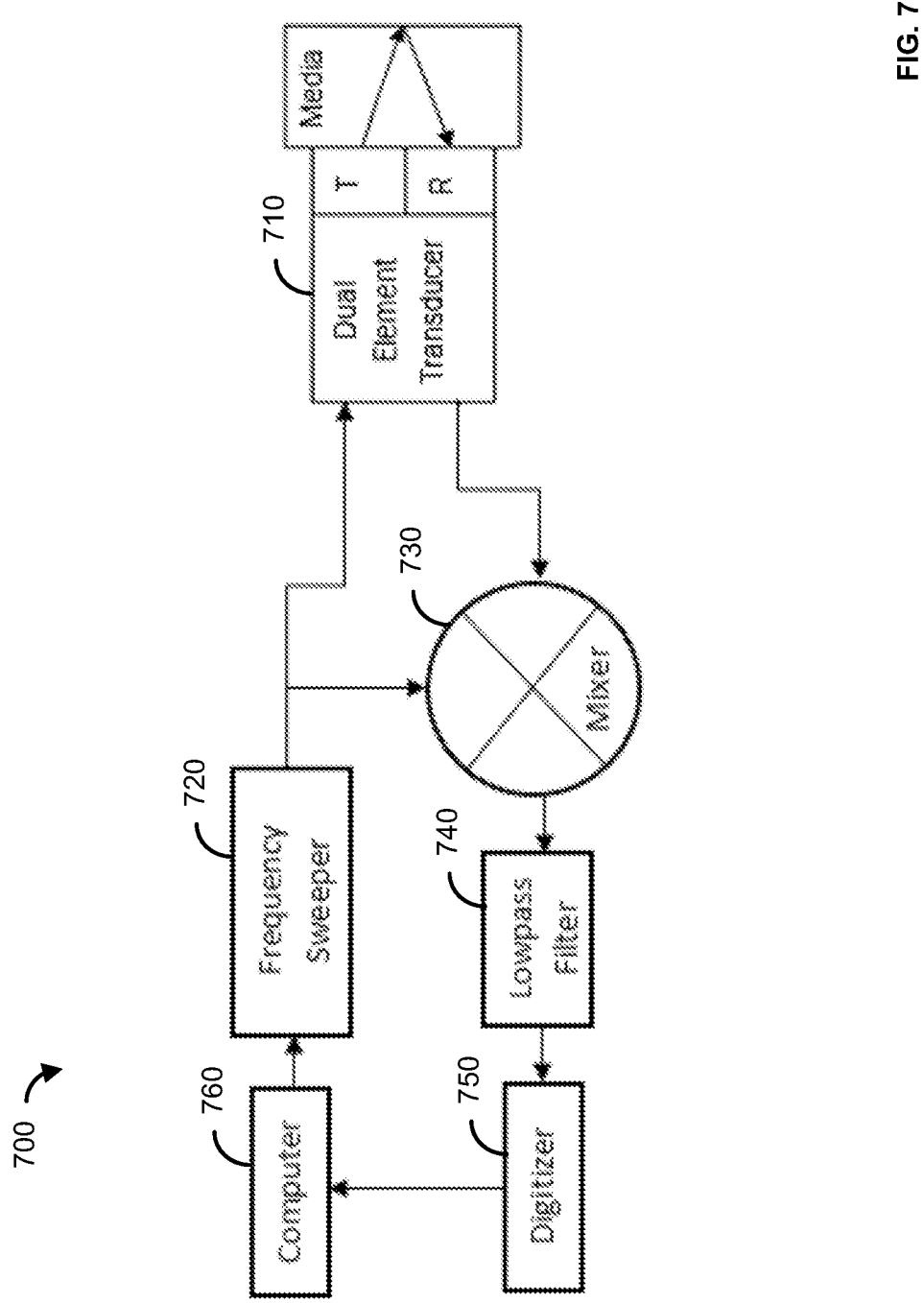
FIG. 7 illustrates a block diagram of a time delay spectrometry setup.

In TDS, a linearly swept (or chirp) transmit signal is used. By linearly sweeping over a range of frequencies in a fixed amount of time, a relationship between time and frequency is implicitly established. Since time of flight of the signal is also directly related to imaging depth (given the speed of sound in the medium), frequency and depth are also implicitly linked by transitivity. This idea of frequency and depth being mathematically linked is the core concept behind TDS. FIG. 7 provides a general schematic of the TDS circuitry and the propagation of the signals of interest (amplifiers omitted for simplification).

The transmitted signal is linearly swept from the frequency $f_{start}$ at t=0 to a frequency $f_{end}$ at t=P. Thus, sweep rate can be defined $S=|f_{start}-f_{end}|/P$ and the instantaneous angular frequency at a given time t can be expressed as:

$$\omega(t)=2\pi f(t)=2\pi f_{start}+2\pi St \quad (1a)$$

This instantaneous "frequency" is the time derivative of the phase and hence by integrating eq. (1a) we obtain:

$$\varphi_T(t) = \varphi_0 + \omega_{start} t + \left(\frac{2\pi}{2}\right)St^2 \text{ for } 0 \le t \le P, \quad (2a)$$

Where $\varphi_0$ is the initial phase at t=0.

The transmitted signal may have an amplitude that varies with the instantaneous frequency depending upon transducer characteristics. The instantaneous frequency depends on the time instant during the sweep and the sweep rate (eq. 1a), so the transmitted signal can be expressed as:

$$T(t) = M_T(t)\cos\left[\varphi_0 + \omega_{start}t + \left(\frac{2\pi}{2}\right)St^2\right] \quad (3a)$$

Where $M_T$ is the effect of the transducer on the transmit signal.

The received signal has a frequency that is the same as the transmitted signal delayed by τ seconds, where τ=D/c, C being the speed of sound in the medium and D being the total length of the acoustic path. As a result of combining this with eq. 1a, the frequency difference between the transmitted and received signals can be expressed as:

$$\Delta\omega = 1\pi SD/c \quad (4a)$$

The received signal can be demodulated, or dechirped by multiplying it by a replica of the signal presently being transmitted. The resulting heterodyned signal, VH(t) is:

$$V_H(t) = M_X \cos\left[\varphi_X + \omega_{start}t + \left(\frac{2\pi}{2}\right)St^2\right] \times \\ M_T M_R \cos\left[\varphi_0 + \varphi_R + \omega_{start}(t-\tau) + \left(\frac{2\pi}{2}\right)S(t-\tau)^2\right] \quad (5a)$$

Where MR(ω) and $\varphi_R$ as the effect of the medium on the signal amplitude and phase respectively, due to the medium and reflector(s).

The output of the heterodyned signal is low pass filtered (LPF) to remove the upper sideband which is comprised of information solely about the transmitted signal and therefore not of interest. The resulting output is:

$$V_{LPF}(t) = \tfrac{1}{2}M_R M_T M_X \cos\left[\varphi_H - 2\pi S\tau t\right] \quad (6a)$$

Where, $\varphi_H$ is the aggregation of all the time-independent terms. The amplitude of this signal is the spectral response, $M_{total} = 0.5 M_R M_T M_X$.

A one-sided Fourier transform (FT), which sorts the data according to frequency will produce an A-scan since the response over the frequency range $f_{start}$ to $f_{end}$ is mapped onto the time axis of this signal from time 0 to P (eq. 1a). This amplitude response is modulated by a frequency Δω, which represents the time delay and therefore the depth (eq. 4a). By applying the FT to the LPF signal and taking its magnitude we get:

$$|\mathcal{F}\{V_{LPF}(t)\}| = \left|M_{total}\left(\omega - \frac{2\pi SD}{c}\right)\right| \quad (7a)$$

Figure 8:
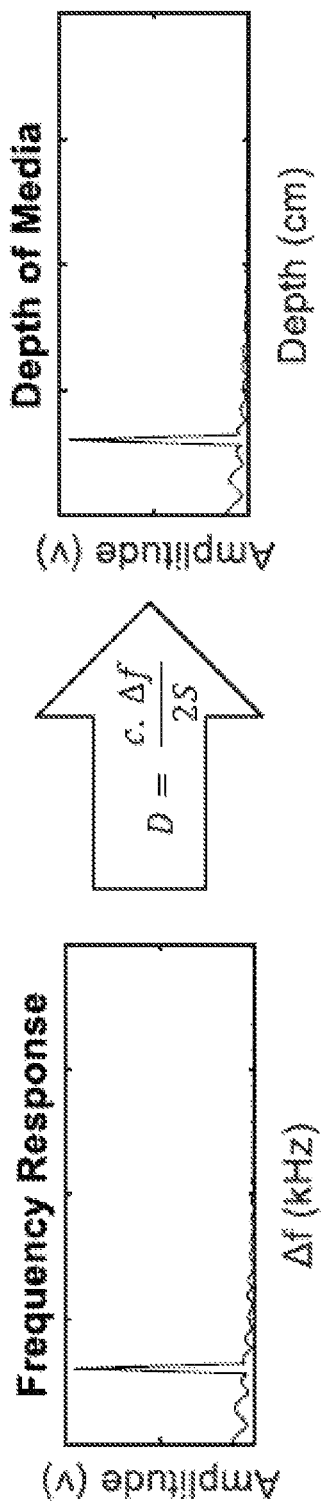
FIG. 8 illustrates an amplitude spectrum of demodulated TDS output to A-mode image conversion.

If the x-axis of the record is rescaled by a factor of 1πSD/c the record will be that of the strength of the reflected signals vs. the distance from the transducer as shown in FIG. 8.

Because TDS is a spread spectrum system and the relationship between frequency, bandwidth and imaging depth is well defined, a bandpass filter can be used to limit imaging to depths of interest. Furthermore, the processing gain, or signal-to-noise improvement, of spread spectrum and other systems is equal to their time-bandwidth products.

Time Delay Spectrometry Hardware

Figure 9:
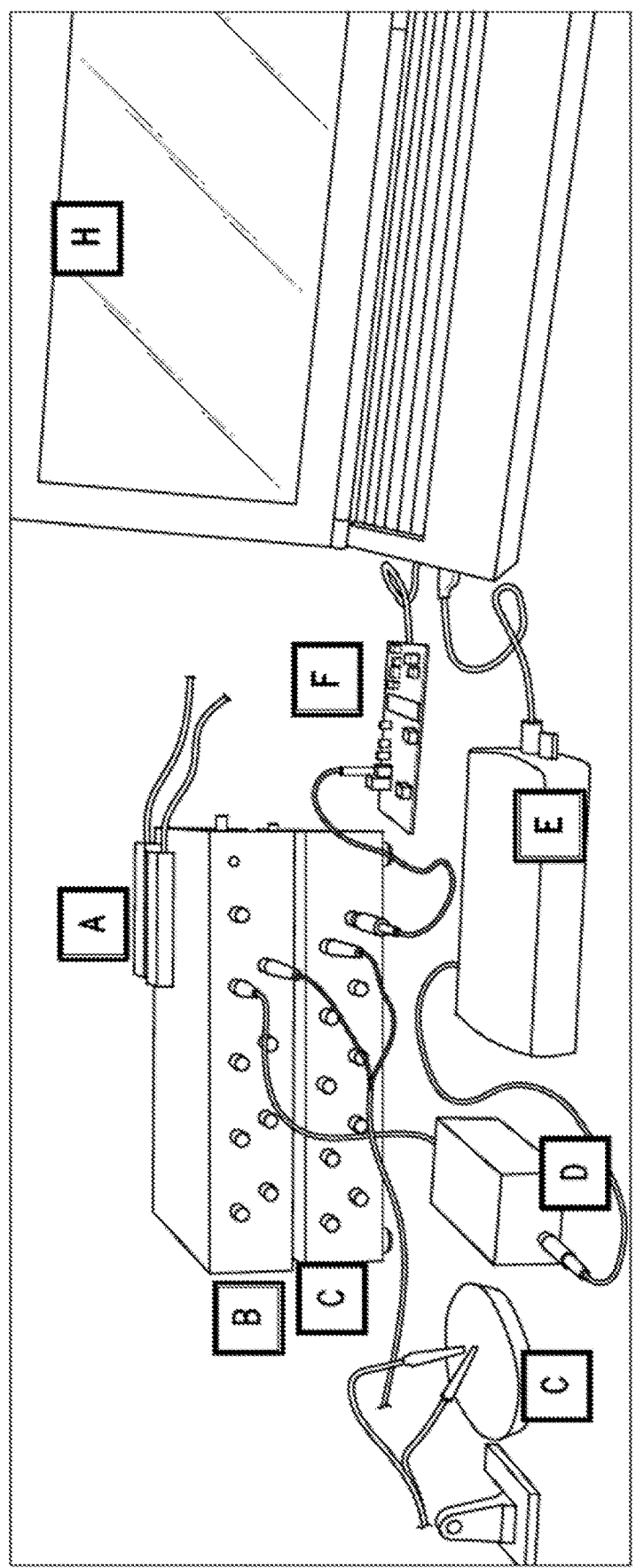
FIG. 9 illustrates a benchtop TDS instrumentation.

The circuit diagram presented in FIG. 7 can be implemented in hardware. A TDS system 700 can comprise a transducer 710, a frequency sweeper 720, a mixer, 730, a demodulator (not shown), an amplifier (not shown), a low-pass filter 740, an analog to digital converter 750, and a computing device 760. These systems components are shown in FIG. 9. FIG. 9 illustrates A) 5V USB battery pack, B) receive amplifier, C) transmit RF amplifier, D) balanced demodulator, E) analog to digital converter, F) AD5930 chirp generator, G) ultrasound transducer, H) laptop. In an example, a programmable frequency sweeper (model AD5930 Analog Devices Inc. Norwood, Mass.) capable of outputting signals ranging from 1 Hz to 25 MHz with an amplitude of 0.5V and sampling rate of 50 MS/s that operates on standard USB power can be used. The frequency sweeps are linear discrete frequency steps with known initial phase. A balanced demodulator for TDS mixing can be used, operating on a 12V D.C. supply. An amplifier can be used amplify both the transmit and receive signals. The amplifier can operate on a dual 5V supply and amplify the transmit signal from the AD5930 to 4.5 VP-P. A low pass filter can be used to isolate the lower side band of the demodulated signal. A cut off frequency of 100 kHz can be selected to ensure that a maximum depth of up to 15 cm could be imaged. The National Instruments USB powered data acquisition device can be used for analog to digital conversion with max sampling rate of 250 kS/s. Further filtering can be performed in MATLAB to select specific depths of interest. In an aspect, a dual element probe can be used, such as a commercially available Olympus 7.5 MHz 6 mm dual element probe (D721-RP). This probe can be "pseudo-focused" at 1.25 cm. However, it is also possible to implement TDS on a single transmit and receive element.

Pulse-Echo Hardware

To perform a direct comparison of the TDS system, the Olympus dual element transducer was used to generate the pulse echo signal with an Olympus 5073PR pulser-receiver at the max energy setting (of 4) and gain set to 5. A Lecroy Waverunner LT344L oscilloscope was utilized to read data for both the TDS and pulse echo experiments.

Experiment

A. Hydrophone Raster Scan

For this experiment, an ONDA AG-2020 Hydrophone was used to scan the TDS and pulse echo beam profile in deionized water. For both scans, a 2-axis servo motor system was utilized. The steps were incremented in 0.01 mm axially and 0.1 mm laterally for a total imaging area of 40×30 mm2. The hydrophone was set to a low gain setting. The scan data were collected on the oscilloscope via a LabVIEW interface.

B. Point Spread Function (PSF)

To calculate both axial and lateral PSF for TDS imaging system and compare it to the one of pulse echo, a set of data were collected from a wire of diameter 0.3 mm. The wire was fixed inside a 60 mm depth water tank with at the depth of 25 mm and served as point target for this experiment. The motor stage was used to move the transducer across the wire with the step increment of 0.05 mm for the distance of 50 mm. The 2D data were collected using oscilloscope.

C. Contrast Phantom

Due to the focal depth of the dual-element transducer, a commercially available contrast phantom could not be used. A custom, agar-based contrast phantom was constructed with 4 agar cylinders containing increasing graphite concentrations from 0.025 g/cm3 to 0.1 g/cm3 in steps of 0.025 g/cm3. This phantom was scanned using the motor stage with step size of 0.02 mm for a total lateral distance of 50 mm.

D. Complex Media

For this experiment, 3 cm of beef tissue was submerged in deionized water. A 50 mm 1D lateral scan was performed with 0.1 mm step size using the motor stage. The scan data were collected on the oscilloscope via a LabVIEW interface.

E. Real Time Imaging with TDS

To evaluate the TDS system in applications which require real time imaging, the data acquisition system was used to stream data into MATLAB. Tissue motion was mimicked by moving the transducer sinusoidally over a 2 cm gel pad, with a peak displacement of 0.5 cm.

Results

The results described below provide a comparison between the TDS and pulse-echo instrumentation. The TDS system used a 5-10 MHz sweep in 20 ms; while the pulse-echo used a pulse repetition frequency of 200 Hz.

TABLE 1

ACOUSTIC INTENSITY OUTPUT FOR TDS & PULSE ECHO

| Parameter [11] | TDS | Pulse echo |
|---|---|---|
| SPTP (mW/cm$^2$) | 109.3 | 179.3 |
| SPTA (mW/cm$^2$) | 10.49 | 0.265 |
| SATA (mW/cm$^2$) | 0.884 | 0.061 |
| SATP (mW/cm$^2$) | 12.94 | 12.39 |
| MI | 0.015 | 0.019 |
| TI (Soft-tissue) | 0.462 | 0.442 |
| Test conditions | 250 kHz/ms, ± 4.5 $V_{P-P}$ | PRF = 200 Hz, 400 $V_{P-P}$ |

Figure 10:
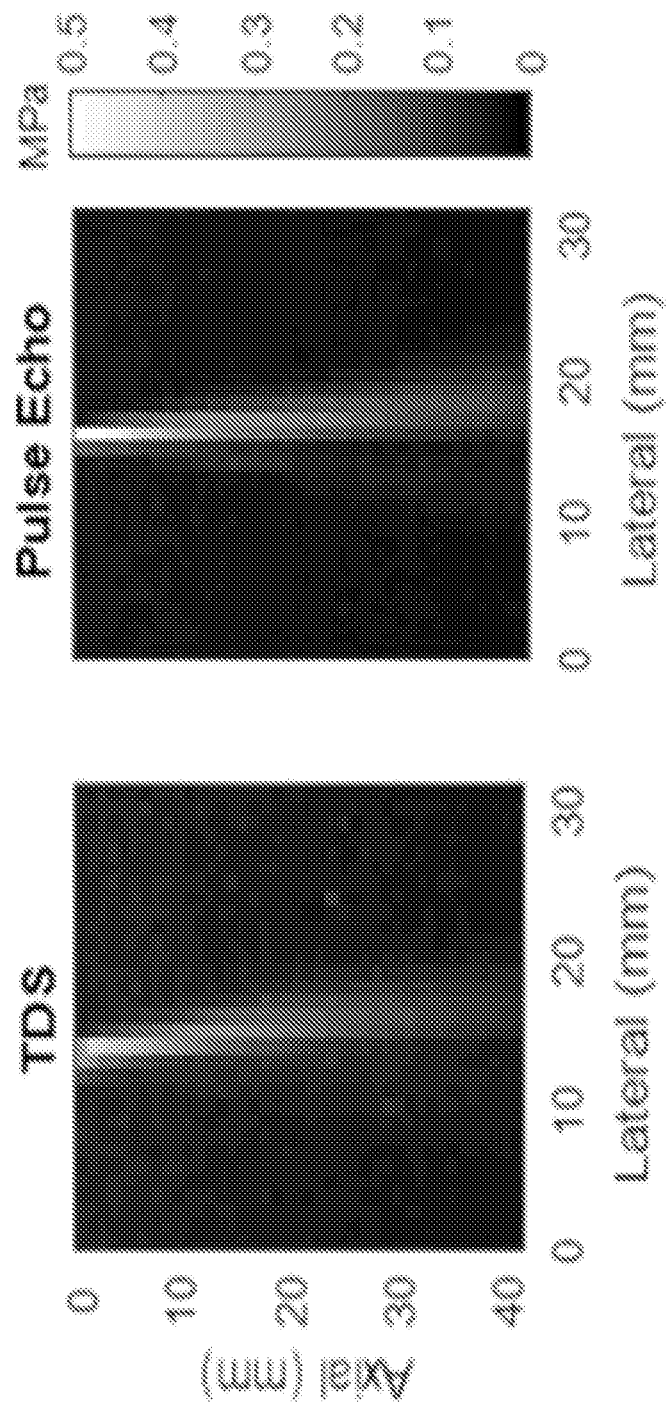
FIG. 10 shows results of a raster scan for TDS and pulse echo setups.

FIG. 10 shows results of the raster scan for TDS and pulse echo setups described in the previous section. The hydrophone raster scans were analyzed in MATLAB and acoustic output measurements and intensity indices have been tabulated in Table 1. Mechanical and thermal indices for TDS and pulse echo were found to be close agreement and well within accepted safe limits. The TDS peak-to-voltage was approximate 10 times lower than pulse echo.

Figure 11:
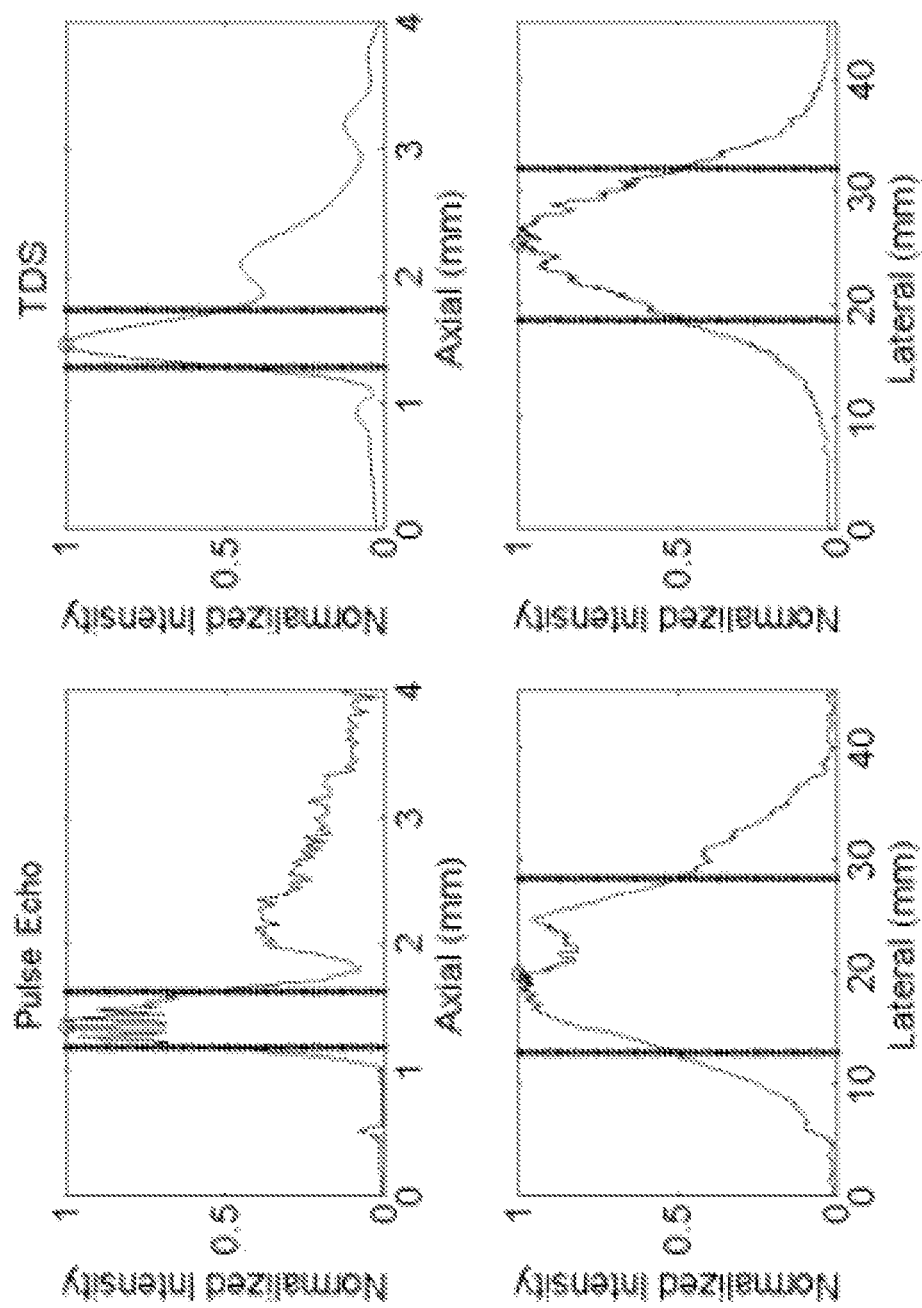
FIG. 11 illustrates lateral and axial point spread functions for TDS and pulse echo.

FIG. 11 illustrates lateral and axial point spread functions for TDS and pulse echo. Point spread functions obtained from wire phantom scans have been compared in FIG. 11. The lateral and axial full-width half-maximum (FWHM) resolutions obtained from PSF for the TDS setup was found to be 13.45 mm and 0.444 mm respectively. For pulse echo, lateral and axial FWHM was measured to be 15.5 mm and 0.440 mm respectively.

Figure 12:
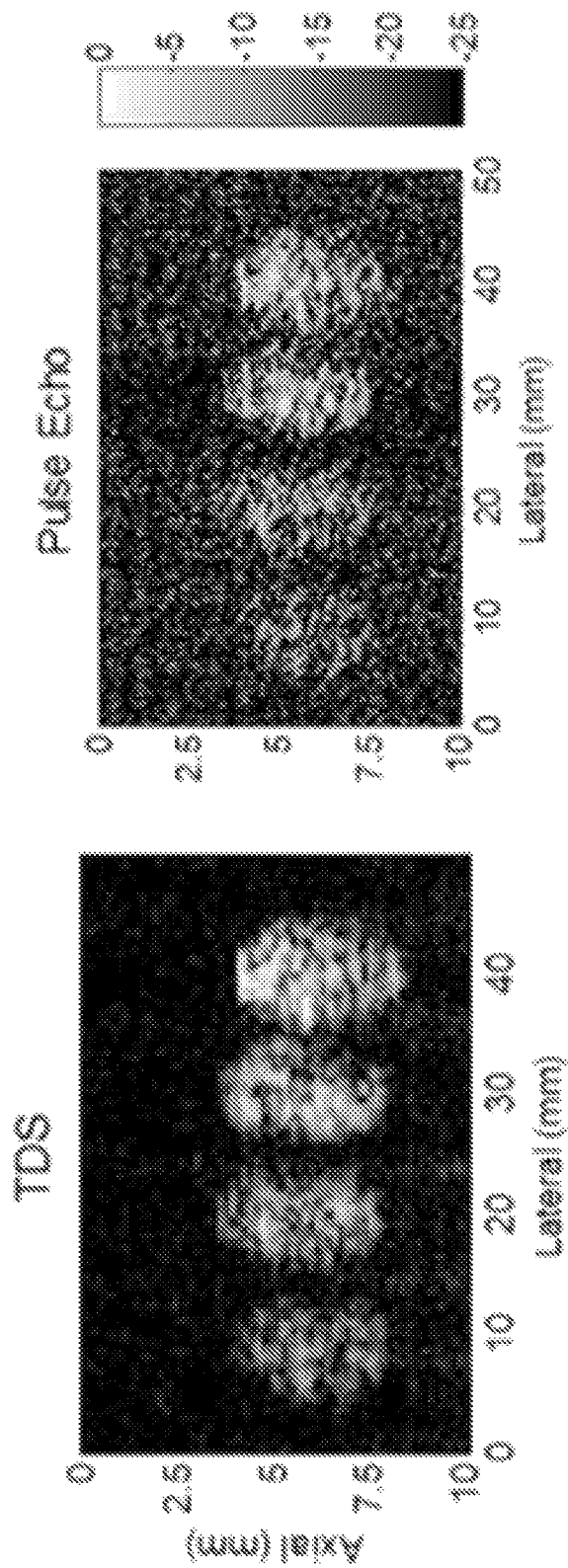
FIG. 12 illustrates contrast phantom images obtained from TDS and pulse echo setup for increasing graphite concentrations (left to right)

FIG. 12 illustrates contrast phantom images obtained from TDS and pulse echo setup for increasing graphite concentrations (left to right). Having established equivalence between TDS and pulse echo in terms of intensity indices and resolution, contrast to noise ratios (CNR) were determined from contrast phantom, B-mode scans shown in FIG. 12 and results have been summarized in Table 2. Worst-case CNR for the lowest graphite concentration (left most) phantom was found to be 0.99 dB for TDS and −2.44 dB for pulse echo.

TABLE 2

CONTRAST TO NOISE RATIOS FOR GRAPHITE LOADED PHANTOMS

| Graphite Conc. | CNR (dB) | |
|---|---|---|
| (g/cm$^3$) | TDS | Pulse echo |
| 0.025 | 0.99 | −2.44 |
| 0.05 | 4.11 | −0.45 |
| 0.075 | 5.18 | 1.25 |
| 0.1 | 6.12 | 2.49 |

Figure 13:
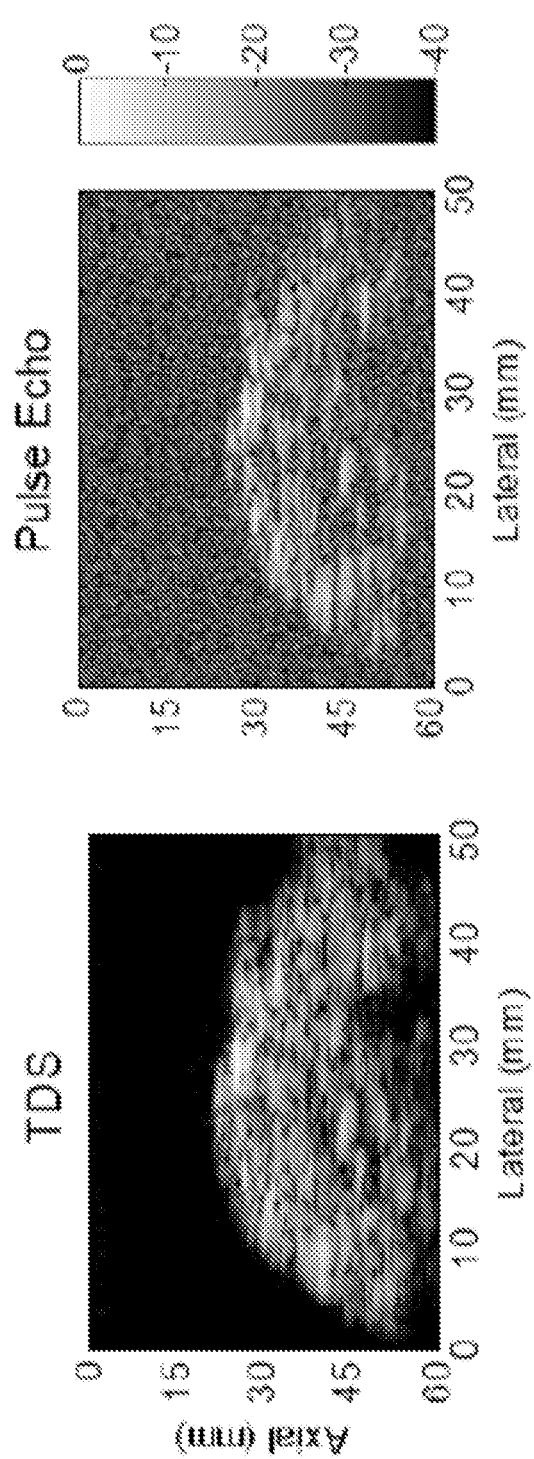
FIG. 13 illustrates a scanned image of 3 cm beef tissue comparing TDS and pulse echo.

CNR was then measured for complex media B-mode images is shown in FIG. 13. FIG. 13 illustrates a scanned image of 3 cm beef tissue comparing TDS and pulseecho. CNR value for TDS was measured to be around 13.7 dB while that of the pulse echo image was 2.3 dB.

Figure 14:
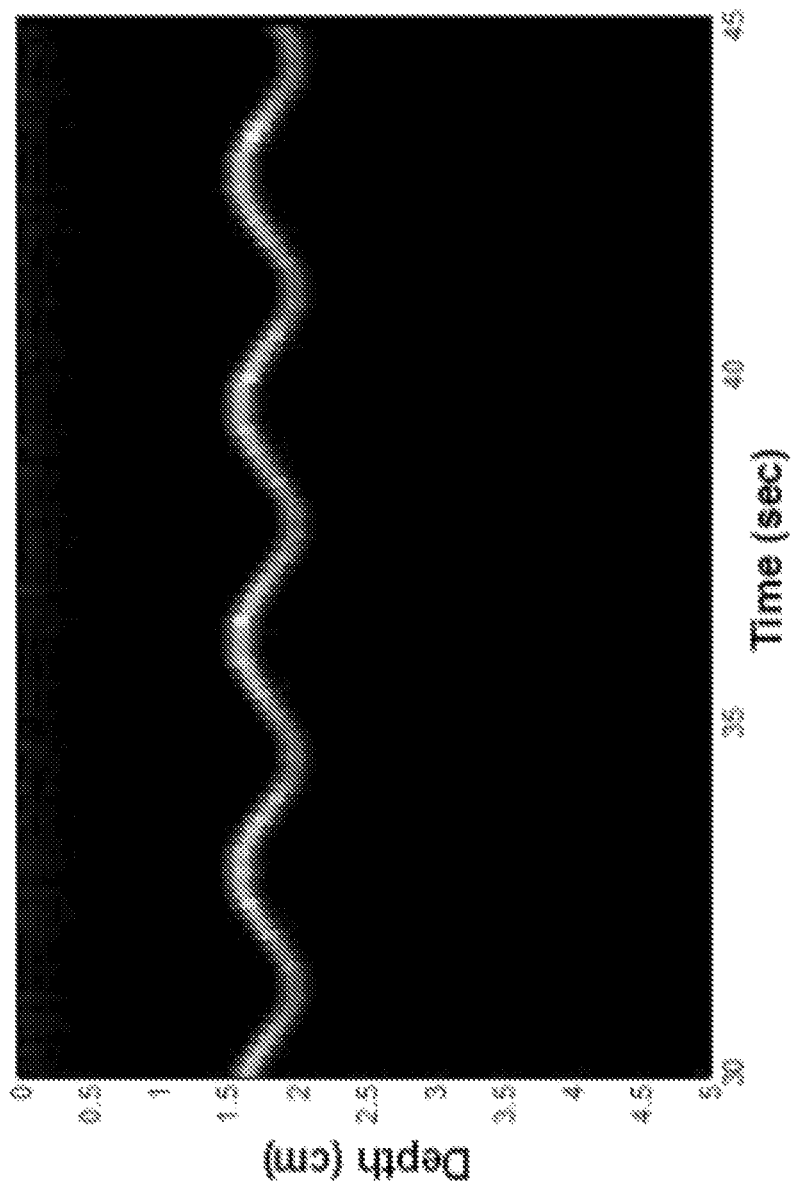
FIG. 14 demonstrates M-mode imaging capabilities of the TDS setup.

FIG. 14 demonstrates M-mode imaging capabilities of the TDS setup. FIG. 14 illustrates a TDS M-mode image showing sinusoidal transducer displacement. The sinusoidal displacement of gel interface corresponding to the physical transducer displacement can be clearly seen in the image.

As demonstrated, time domain spectrometry is an alternative, low-voltage signaling paradigm to pulse echo. A-mode images can be directly generated from the amplitude spectrum of demodulated TDS signal reducing computational burden compared to pulse echo systems. The benchtop TDS hardware setup was compared against a commercially available pulser-receiver. For equivalent mechanical and thermal indices, TDS was found to have significantly higher CNR compared to pulse echo, making it suitable for applications requiring low acoustic output such as long-term monitoring applications. M-mode images obtained from the benchtop system demonstrate the feasibility of TDS as a real-time imaging modality.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method comprising:
    transmitting, from a source via a transmit channel of a transducer, a swept frequency signal through a medium;
    determining, based on a time delay associated with the swept frequency signal, a plurality of frequencies, wherein the time delay associated with the swept frequency signal is based on the swept frequency signal propagating through the medium;
    determining, based on:
        one or more components of the swept frequency signal received via a receive channel of the transducer,
        a low-pass filter, and
        a range, one or more frequencies associated with the swept frequency signal, wherein the one or more components comprise a sum-frequency component and a difference-frequency component, and wherein the low-pass filter is configured to filter one or more of the sum-frequency component or the difference-frequency component; and determining, based on the one or more frequencies and a steering angle, an image.

2. The method of claim 1, wherein the image is an electrical representation of a region of interest associated with the medium.

3. The method of claim 1, wherein the medium is a tissue.

4. The method of claim 1, wherein determining the one or more frequencies associated with the swept frequency signal comprises a Fourier Transformation of at least a portion of the swept frequency signal.

5. The method of claim 1, wherein the swept frequency signal comprises a voltage of five volts or less.

6. The method of claim 1, wherein the image is determined in real-time.

7. The method of claim 1, wherein the transmit channel of the transducer comprises a two-channel transmit element and the receive channel of the transducer comprises a 4-channel receive element.

8. The method of claim 1, wherein the range comprises frequencies associated with audio frequencies.

9. An apparatus comprising:
one or more processors;
a transducer; and
memory storing processor executable instructions that, when executed by the one or more processors, cause the apparatus to:
transmit, via a transmit channel of the transducer, a swept frequency signal through a medium;
determine, based on a time delay associated with the swept frequency signal, a plurality of frequencies, wherein the time delay associated with the swept frequency signal is based on the swept frequency signal propagating through the medium;
determine, based on:
one or more components of the swept frequency signal received via a receive channel of the transducer,
a low-pass filter, and
a range,
one or more frequencies associated with the swept frequency signal, wherein the one or more components comprise a sum-frequency component and a difference-frequency component, and wherein the low-pass filter is configured to filter one or more of the sum-frequency component or the difference-frequency component;
and determine, based on the one or more frequencies and a steering angle, an image.

10. The apparatus of claim 9, wherein the image is an electrical representation of a region of interest associated with the medium.

11. The apparatus of claim 9, wherein the medium is a tissue.

12. The apparatus of claim 9, wherein determining the one or more frequencies associated with the swept frequency signal comprises a Fourier Transformation of at least a portion of the swept frequency signal.

13. The apparatus of claim 9, wherein the swept frequency signal comprises a voltage of five volts or less.

14. The apparatus of claim 9, wherein the image is determined in real-time.

15. The apparatus of claim 9, wherein the transmit channel of the transducer comprises a two-channel transmit element and the receive channel of the transducer comprises a 4-channel receive element.

16. The apparatus of claim 9, wherein the range comprises frequencies associated with audio frequencies.

17. A system comprising
a signal source configured to produce a swept frequency signal;
a dual element transducer configured to:
transmit, via a one or more transmission channels, the swept frequency signal through a medium; and
receive, via a one or more receiving channels, one or more components of the swept frequency signal, wherein the one or more components comprise a sum-frequency component, a difference-frequency component, and a time delay;
one or more mixers configured to output the sum-frequency component and the difference-frequency component;
one or more low pass filters configured to filter the swept frequency signal by filtering one or more of the sum-frequency component or the difference-frequency component; and
a digital signal processor configured:
to process the filtered swept frequency signal; and
generate, based on the processing, an image.

18. The system of claim 17, wherein the image is an electrical representation of a region of interest associated with the medium.

19. The system of claim 17, wherein the medium is a tissue.

20. The system of claim 17, wherein the image is determined in real-time.

* * * * *

UNITED STATES PATENT AND TRADEMARK OFFICE
CERTIFICATE OF CORRECTION

PATENT NO.       : 10,935,645 B2
APPLICATION NO.  : 15/793969
DATED            : March 2, 2021
INVENTOR(S)      : Sikdar et al.

Page 1 of 1

It is certified that error appears in the above-identified patent and that said Letters Patent is hereby corrected as shown below:

In the Specification

IN THE DETAILED DESCRIPTION
Column 1, Lines 13-15 should read:
This invention was made with government support under CNS1329829 awarded by the National Science Foundation and under W81XWH-16-1-0722 awarded by US Army Medical Research Acquisition Activity. The government has certain rights in the invention.

Signed and Sealed this
Sixth Day of April, 2021

Drew Hirshfeld
*Performing the Functions and Duties of the
Under Secretary of Commerce for Intellectual Property and
Director of the United States Patent and Trademark Office*